US012643873B2

(12) United States Patent
Herblot et al.

(10) Patent No.: US 12,643,873 B2
(45) Date of Patent: Jun. 2, 2026

(54) XANTHENE DERIVATIVES, MIXTURES COMPRISING SAME, MANUFACTURING METHOD AND CORRESPONDING USES

(71) Applicant: ARKEMA FRANCE, Colombes (FR)

(72) Inventors: Martin Herblot, Serquigny (FR); Julien Jouanneau, Pierre-Benite Cedex (FR); Guillaume Le, Serquigny (FR)

(73) Assignee: ARKEMA FRANCE, Puteaux (FR)

( * ) Notice: Subject to any disclaimer, the term of this patent is extended or adjusted under 35 U.S.C. 154(b) by 768 days.

(21) Appl. No.: 17/998,972

(22) PCT Filed: May 14, 2021

(86) PCT No.: PCT/FR2021/050841
§ 371 (c)(1),
(2) Date: Nov. 16, 2022

(87) PCT Pub. No.: WO2021/234251
PCT Pub. Date: Nov. 25, 2021

(65) Prior Publication Data

US 2023/0174498 A1 Jun. 8, 2023

(30) Foreign Application Priority Data

May 19, 2020 (FR) ...................................... 2005059

(51) Int. Cl.
*C07D 311/86* (2006.01)
*C09K 11/06* (2006.01)

(52) U.S. Cl.
CPC ............ *C07D 311/86* (2013.01); *C09K 11/06* (2013.01); *C09K 2211/1018* (2013.01)

(58) Field of Classification Search
CPC .................................................... C07D 311/86
See application file for complete search history.

(56) References Cited

U.S. PATENT DOCUMENTS 3,065,205 A * 11/1962 Bonner, Jr. ............ C08G 61/00 528/196
4,329,461 A 5/1982 Khanna et al.
(Continued)

FOREIGN PATENT DOCUMENTS

CN 110437427 * 11/2019
EP 0515133 A2 11/1992
(Continued)

OTHER PUBLICATIONS

A Common Diaryl Ether Intermediate for the Gram-Scale Synthesis of Oxazine and Xanthene Fluorophores, Andrew V. Anzalone et al., Angewandte Communications, vol. 52, pp. 650-654.
(Continued)

*Primary Examiner* — Valerie Rodriguez-Garcia
(74) *Attorney, Agent, or Firm* — Boone IP Law

(57) ABSTRACT

A xanthene derivative of formula I or of formula II, which may be useful as a chromophore, as a free-radical generator, or as an adhesion promoter and/or coupling agent. A mixture including the xanthene derivative of formula I or of formula II. A process for preparing the xanthene derivative process involving reacting a compound of formula (III) with a compound of formula (IVa) or (IVb), in the presence of a Lewis acid. A process for preparing the mixture including the xanthene derivative of formula I or of formula II.

7 Claims, 4 Drawing Sheets

(56) References Cited

U.S. PATENT DOCUMENTS

| | | | | |
|---|---|---|---|---|
| 2011/0159603 | A1 | 6/2011 | Nagano et al. | |
| 2019/0077739 | A1* | 3/2019 | Jouanneau | C07C 45/80 |

FOREIGN PATENT DOCUMENTS

| | | | |
|---|---|---|---|
| WO | WO 2018-211045 | * | 11/2018 |
| WO | 2020094819 | A1 | 5/2020 |

OTHER PUBLICATIONS

First Office Action with English translation only, mailed on Apr. 19, 2024, by the China National Intellectual Property Administration for Chinese Application No. (202180034672.2), 11 pages.

Arnett, E. M. et al."Energetics of Formation for Conjugate Xanthyl Carbenium Ions, Carbanions, and Radicals by Hydride, Proton, and Electron Transfer in Solution and Their Reactions to Give Symmetrical Bixanthyls" J. Am. Chem. Soc., 1993, vol. 115, pp. 12603-12604.

Sarma, D. et al."Visible-light induced enhancement in the multicatalytic activity of sulfated carbon dots for aerobic carbon-carbon bond formation" Green Chem, 2019, vol. 21, pp. 6717-6126.

Kotaskova, M."Synthesis of New Xanthene Derivatives" 2013, 174 pages.

International Search Report (PCT/ISA/210) with English translation and Written Opinion (PCT/ISA/237) mailed on Jul. 29, 2021, by the European Patent Office as the International Searching Authority for International Application No. PCT/FR2021/050841.

* cited by examiner

[Fig. 1]
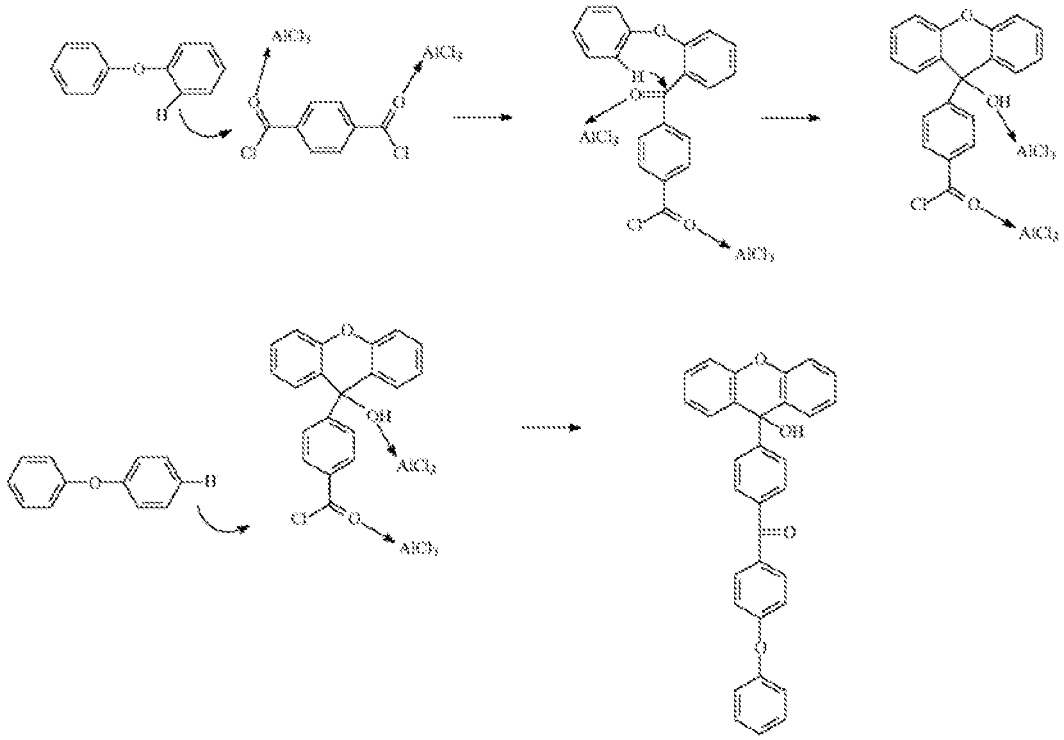
[Fig. 2]
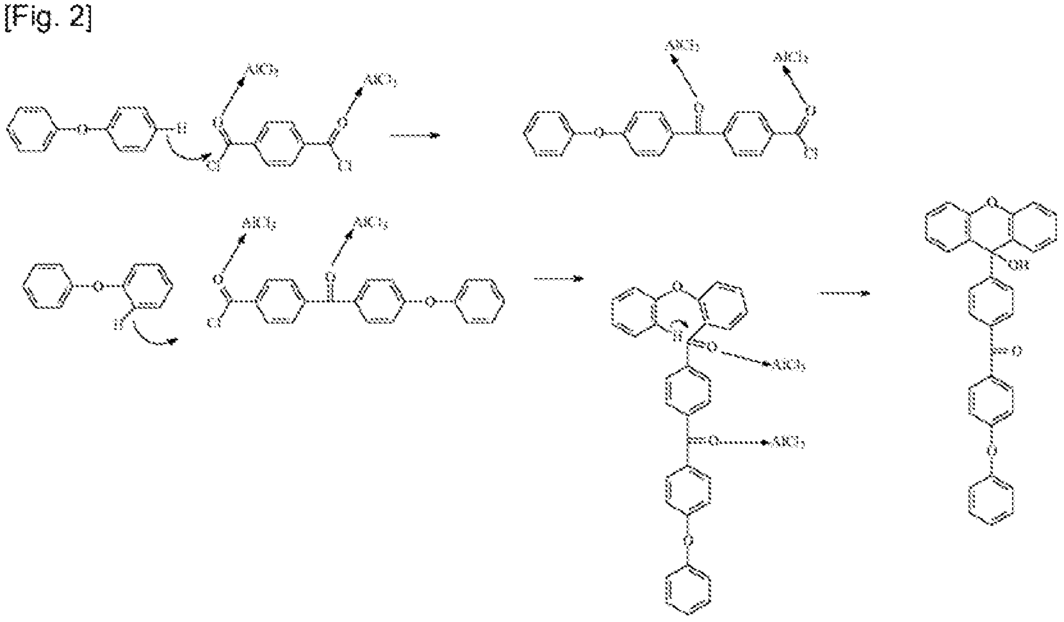

[Fig. 3]
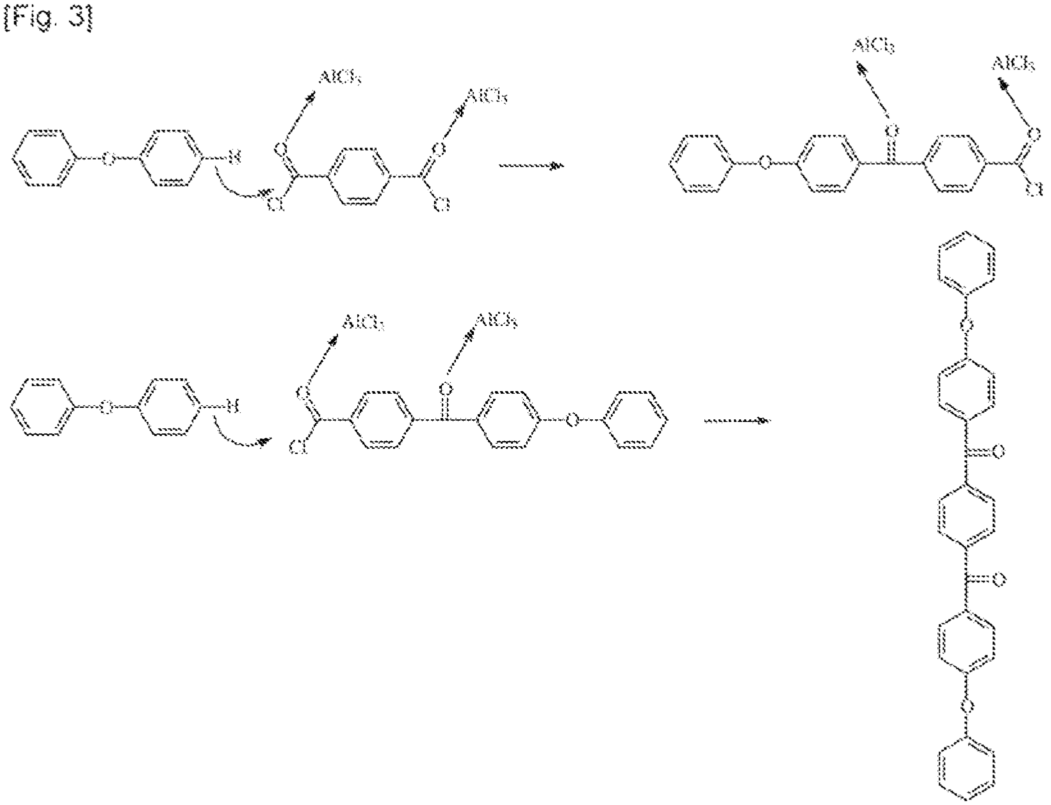
[Fig. 4]
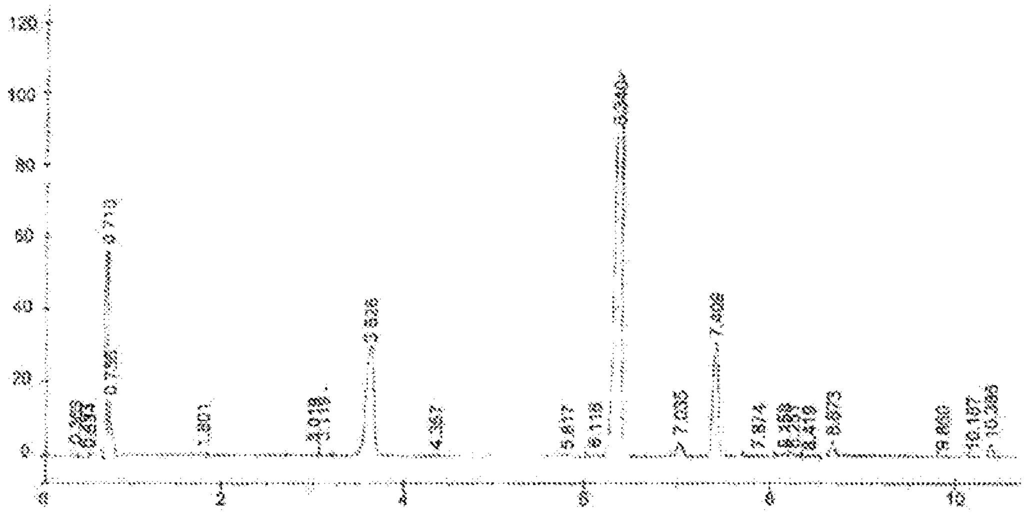

[Fig. 5]
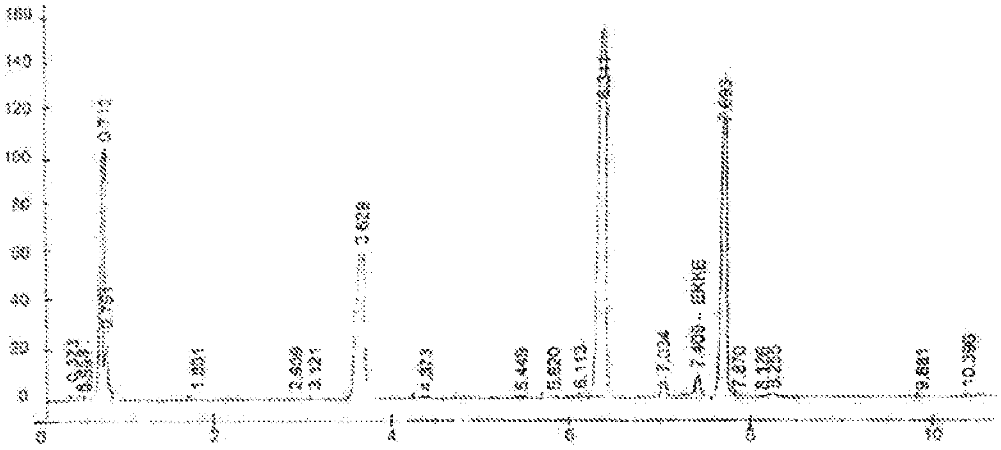
[Fig. 6]
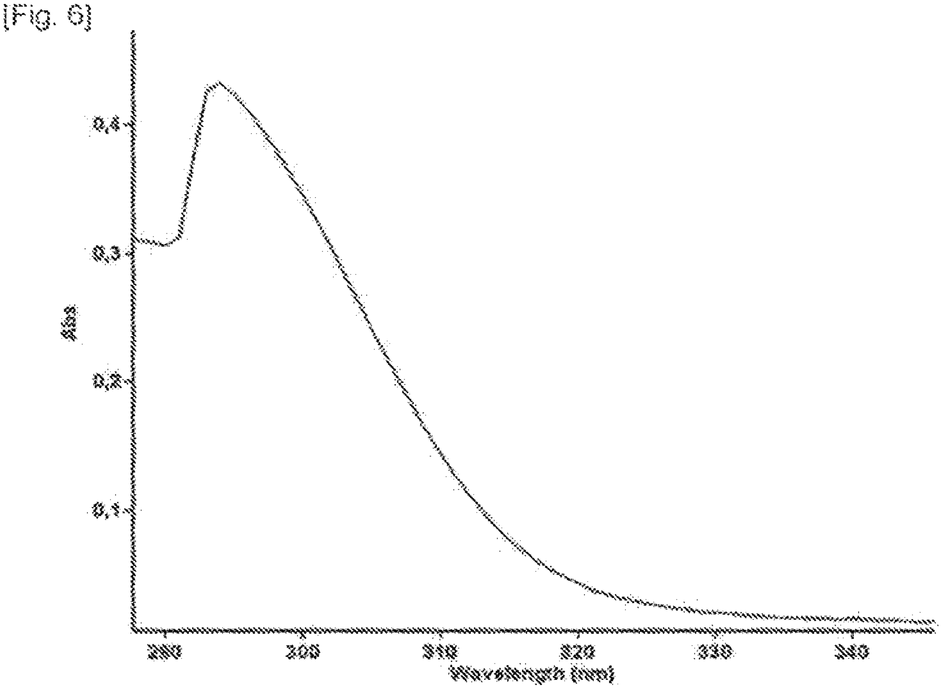

[Fig. 7]
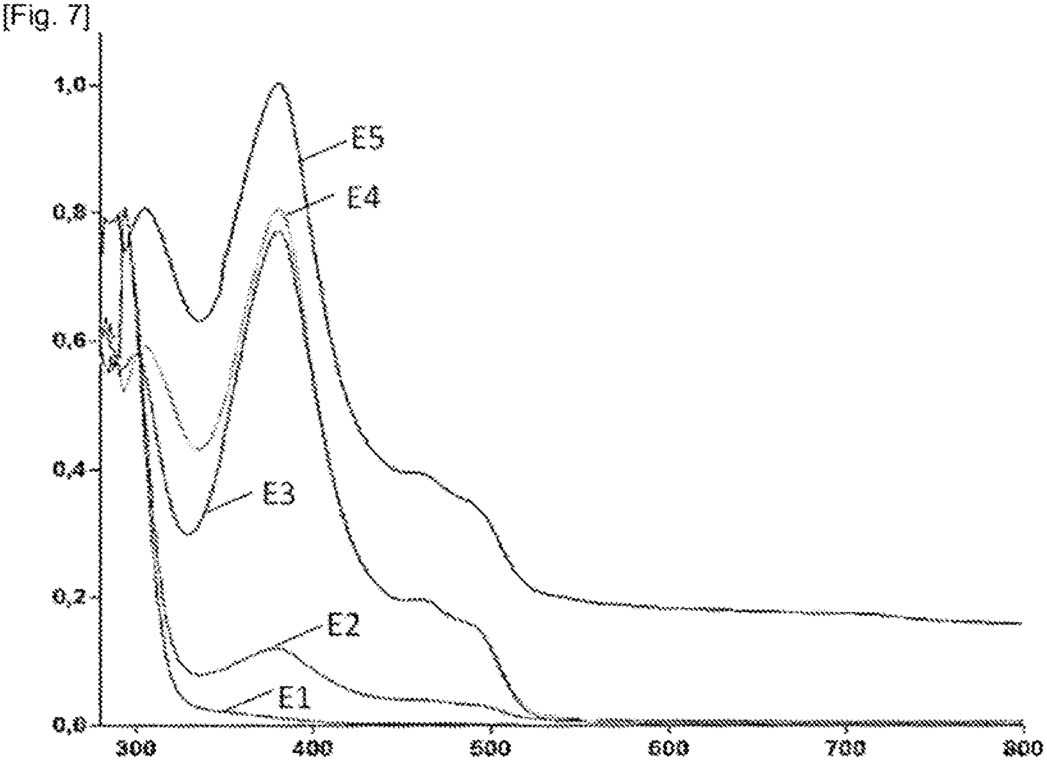

XANTHENE DERIVATIVES, MIXTURES COMPRISING SAME, MANUFACTURING METHOD AND CORRESPONDING USES

TECHNICAL FIELD

The invention relates to the field of xanthene derivatives. More particularly, the invention relates to a family of particular xanthene derivatives, to a process for manufacturing same and also to corresponding uses.

PRIOR ART

Xanthene and its derivatives are known as chromophores. Xanthene has the chemical formula:

[Chem 1]

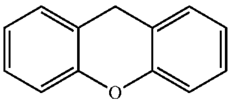

(D)

A derivative of xanthene that is particularly known for its fluorescent properties is fluorescein, of chemical formula:

[Chem 2]

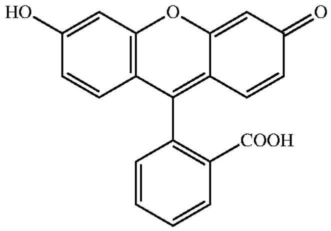

(DI)

Fluorescein and its derivatives have been used in many fields, notably as tracers for coloring water or as markers of biological molecules (peptides, antibodies, nucleotides, oligonucleotides, hormones, lipids, etc.). In the case of its use as a marker of biological molecules, fluorescein or its derivatives are generally grafted by covalent bonding to the molecule of interest usually by means of a group reacting with the amine functions.

The synthesis of many other xanthene derivatives, according to more or less complex reaction schemes, is known from the prior art: see, for example, the doctoral thesis: Kotásková, Michaela. *Synthesis of new xanthene derivatives.* 2013.

OBJECTS OF THE INVENTION

The object of the invention is to propose a novel family of xanthene derivatives and also several associated uses.

According to at least certain embodiments, the object is to propose compounds which have fluorescence properties.

According to at least certain embodiments, the object is to propose compounds which can be used as radical initiators.

According to at least certain embodiments, the object is to propose compounds for improving the adhesion of an aromatic or semiaromatic polymeric matrix with a substrate.

According to at least certain embodiments, the object of the invention is to propose compounds for improving the compatibility between one aromatic or semiaromatic polymeric matrix and another aromatic, semiaromatic, or aliphatic polymeric matrix.

The object of the invention is also to propose a process for manufacturing this novel family of xanthene derivatives.

The object of the invention is also to propose possible uses for this novel family of derivatives.

SUMMARY OF THE INVENTION

The invention relates to a compound having the chemical formula:

[Chem 3]

(I)

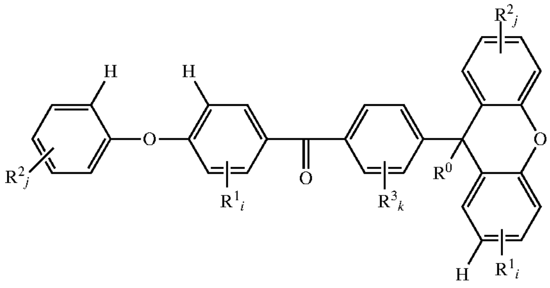

or

[Chem 4]

(II)

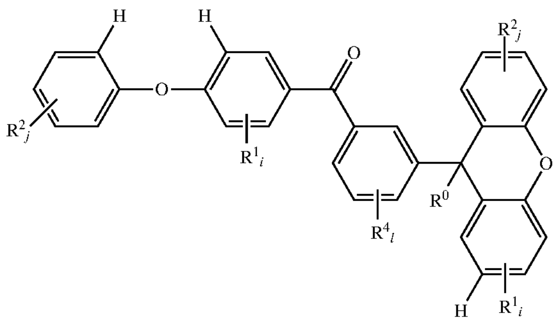

in which:

$R^0$ denotes: a charge +, —H or —OH;

i is an integer having a value from 0 to 3;

j, k and l are integers independently having a value from 0 to 4;

for any i, $$R_i^1,$$

for any j, $$R_j^2,$$

for any k, $R_k^3$, for any l, $R_l^4$ are independently chosen from the list consisting of:

alkyl, alkenyl, alkynyl, aryl, ether, thioether, carboxylic acid, ester, notably carboxylic ester, amide, notably primary amide, halogen, imide, nitro and aliphatics comprising a nitro function, nitrile and aliphatics comprising a nitrile function, carbonyl, alkali metal or alkaline-earth metal sulfonate, alkyl sulfonate, alkali metal or alkaline-earth metal phosphonate, amine, and quaternary ammonium.

According to certain embodiments, said i, j, k and l are all equal to 0.

According to certain embodiments, $R^0$ is: —OH.

According to certain embodiments, $R^0$ is: —H.

According to certain embodiments, $R^0$ is: +.

The invention also relates to a process for notably obtaining the compound of formulae (I) and/or (II). The process involves reacting a compound of formula (III) with a compound of formula (IVa) or (IVb), in the presence of a Lewis acid. Compound (III) has the chemical formula:

[Chem 5]

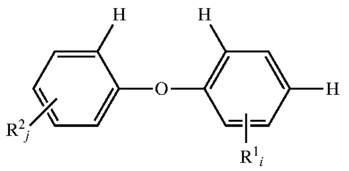

Compound (IVa) has the chemical formula:

[Chem 6]

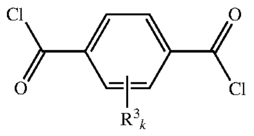

Compound (IVb) has the chemical formula:

[Chem 7]

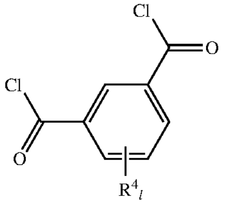

in which i, j, k, l, $R_i^1$, $R_j^2$, $R_k^3$ and $R_l^4$ are defined as above;

to obtain a product mixture comprising a compound as described above.

According to certain embodiments, said i, j, k and l are all equal to 0.

According to certain embodiments, the reaction of the compound of formula (III) with the compound of formula (IVa) or, respectively, of formula (IVb) is performed in a reaction solvent. The reaction solvent is preferentially an aprotic solvent. The reaction solvent is more preferably chosen from the group consisting of: dichloromethane, carbon disulfide, ortho-dichlorobenzene, meta-dichlorobenzene, para-dichlorobenzene, 1,2,4-trichlorobenzene, 1,2,3-trichlorobenzene, ortho-difluorobenzene, 1,2-dichloroethane, 1,1-dichloroethane, 1,1,2,2-tetrachloroethane, tetrachloroethylene, dichloromethane, nitrobenzene and a mixture thereof. The reaction solvent is most preferably ortho-dichlorobenzene.

According to certain embodiments, the Lewis acid is chosen from the group consisting of: aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride and molybdenum pentachloride. Preferentially, the Lewis acid is chosen from the group consisting of: aluminum trichloride, boron trichloride, aluminum tribromide, titanium tetrachloride, antimony pentachloride, ferric chloride, gallium trichloride and molybdenum pentachloride. More preferably, the Lewis acid is aluminum trichloride.

According to certain embodiments, the molar amount of compound of formula (III) relative to the molar amount of compound of formula (IVa) or, respectively, (IVb) is from 2 to 6. Preferably, the molar amount of compound of formula (III) relative to the molar amount of compound of formula (IVa) or, respectively, (IVb) is from 2 to 4.

According to certain embodiments, the molar amount of Lewis acid relative to the sum of the molar amounts of compound of formula (III) and compound of formula (IVa) or, respectively, (IVb) is from 0.25 to 2. Preferably, the molar amount of compound of formula (III) relative to the molar amount of compound of formula (IVa) or, respectively, (IVb) is from 0.3 to 1.5.

According to certain embodiments, the process comprises:

at least one step of separating the compound of formula (I) or, respectively, of formula (II) from at least one other species of the product mixture; and, optionally at least one step of purifying the compound of formula (I) or, respectively, of formula (II).

According to certain embodiments, the process comprises a solid/liquid separation step in order to recover a liquid comprising in major amount the compound of formula (I) or, respectively, of formula (II), and a wet cake comprising in minor amount the compound of formula (I) or, respectively, of formula (II).

The invention also relates to a mixture of compounds comprising:

the compound of formula (I) as described above;

a compound of formula:

According to certain embodiments, in this mixture, the compound of formula (II) represents from 0.01 mol % to 10 mol % relative to the total number of moles of the compounds of formulae (II), (X-i) and (X-ii).

[Chem 8]

(IX-i)

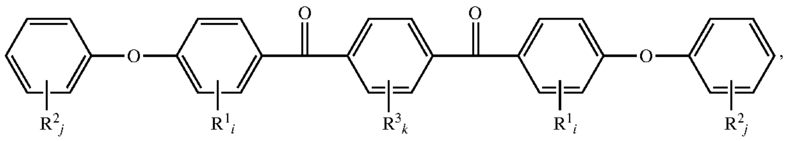

[Chem 9]

(IX-ii)

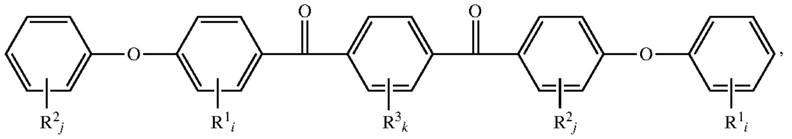

or a mixture thereof, in which i, j, k, $R_i^1$, $R_j^2$ and $R_k^3$ are defined such as those of compound (I).

According to certain embodiments, in this mixture, the compound of formula (I) represents from 0.01 mol % to 10 mol % relative to the total number of moles of the compounds of formulae (I), (IX-i) and (IX-ii).

According to certain embodiments, in this mixture, the compound of formula (I) represents from 90 mol % to 99.99 mol % relative to the total number of moles of the compounds of formulae (I), (IX-i) and (IX-ii).

The invention also relates to a mixture of compounds comprising:

the compound of formula (II) as described;

a compound of formula:

[Chem 10]

(X-i)

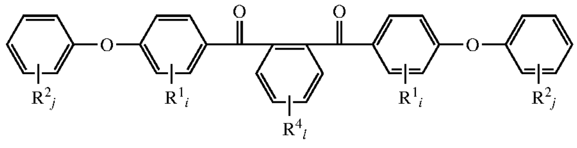

[Chem 11]

(X-ii)

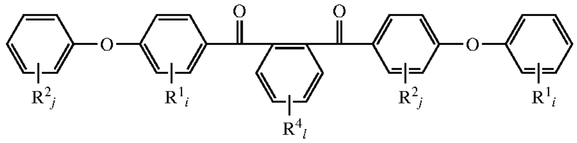

or a mixture thereof, in which i, j, l, $R_i^1$, $R_j^2$ and $R_l^4$ are defined such as those of compound (II).

According to certain embodiments, in this mixture, the compound of formula (II) represents from 90 mol % to 99.99 mol % relative to the total number of moles of the compounds of formulae (II), (X-i) and (X-ii).

Finally, the invention relates to the use of a compound of formula (I) or (II) as a chromophore, as a free-radical generator, or as an adhesion promoter and/or coupling agent.

LIST OF FIGURES

FIG. 1 represents a first reaction scheme for obtaining the desired compound of formula (V) from a mixture of diphenyl ether and terephthaloyl chloride in the presence of aluminum trichloride.

FIG. 2 represents an alternative reaction scheme to that shown in FIG. 1 for obtaining the desired compound of formula (V) from a mixture of diphenyl ether and terephthaloyl chloride in the presence of aluminum trichloride.

FIG. 3 represents a reaction scheme for obtaining the compound of formula (VIII), obtained from the predominantly competing reaction, from a mixture of diphenyl ether and terephthaloyl chloride in the presence of aluminum trichloride.

FIG. 4 represents the HPLC/MS chromatogram of the mixture obtained according to Example 1, containing essentially the compound of formula (V). The x-axis represents an elution time and is expressed in minutes (min). The y-axis represents the ion abundance and is expressed in milli-arbitrary units (mAU).

FIG. 5 represents the mass spectrum of the mixture obtained according to Example 1 containing essentially the compound of formula (VI) by HPLC/MS. The x-axis represents an elution time and is expressed in minutes (min). The y-axis represents the ion abundance and is expressed in milli-arbitrary units (mAU).

FIG. 6 represents the UV/IR absorbance spectrum of the compound of formula (V). The x-axis represents the wavelengths, expressed in nanometers (nm). The y-axis represents the absorbance (dimensionless).

FIG. 7 represents the UV/IR absorbance spectrum of the compound in the (V) form and/or in the (VI) form at different pH values. The x-axis represents the wavelengths, expressed in nanometers (nm). The y-axis represents the absorbance (dimensionless).

DETAILED DESCRIPTION OF THE INVENTION

The invention will now be described in greater detail and in a nonlimiting manner in the description that follows.

The process involves reacting a compound of formula (III) with a compound of formula (IVa) or, respectively, of formula (IVb), in the presence of a Lewis acid;

compound (III) being an aromatic ether having the chemical formula:

[Chem 12]

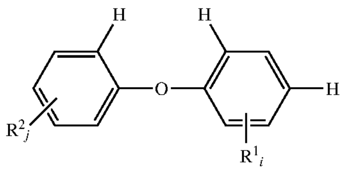

compound (IVa) being an aromatic acyl chloride having the chemical formula:

[Chem 13]

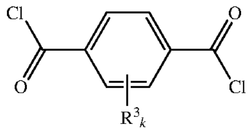

and the compound of formula (IVb) being an aromatic acyl chloride having the chemical formula:

[Chem 14]

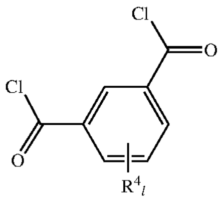

in which:

i is an integer having a value from 0 to 3;

j, k and l are integers independently having a value from 0 to 4;

for any i, $R^1_i$, for any j, $R^2_j$, for any k, $R^3_k$, for any l, $R^4_l$ are independently chosen from the list consisting of: alkyl, alkenyl, alkynyl, aryl, ether, thioether, carboxylic acid, ester, notably carboxylic ester, amide, notably primary amide, halogen, imide, nitro and aliphatics comprising a nitro function, nitrile and aliphatics comprising a nitrile function, carbonyl, alkali or alkaline-earth metal sulfonate, alkyl sulfonate, alkali metal or alkaline-earth metal phosphonate, amine and quaternary ammonium.

Preferentially, in the preceding formulae, for any i, $R^1_i$, for any j, $R^2_j$, for any k, $R^3_k$, for any l, $R^4_l$ are independently chosen from the list consisting of: alkyl, aryl, ether, thioether, carboxylic acid, ester, notably carboxylic ester, amide, notably primary amide, imide, nitro and aliphatics comprising a nitro function, nitrile and aliphatics comprising a nitrile function, carbonyl, alkali metal or alkaline-earth metal sulfonate, alkyl sulfonate, alkali metal or alkaline-earth metal phosphonate, and tertiary amine.

According to this notation, $R^i_0$ means that the benzene group on which the latter is positioned has no substituent;

$R^i_1$ means that the benzene group on which the latter is positioned comprises exactly one substituent;

$R_2^i$ means that the benzene group on which the latter is positioned comprises exactly two substituents, each of the two substituents possibly being chosen independently of each other, etc. In certain embodiments, the process involves reacting diphenyl ether with terephthaloyl chloride or isophthaloyl chloride in the presence of a Lewis acid, for example aluminum trichloride ($AlCl_3$).

Without wishing to be bound by theory, the inventors believe that the reaction for obtaining compounds according to the invention takes place according to the reaction scheme in FIG. 1 and/or according to the reaction scheme in FIG. 2. For simplicity, the reaction schemes in FIGS. 1 and 2 represent the example of a mixture of diphenyl ether and terephthaloyl chloride in the presence of aluminum trichloride, but are not intended to be limiting to these compounds alone. The ortho and para positions of the phenyl groups of diphenyl ether are particularly activated by the mesomeric effect, which would explain why the electrophilic substitutions take place mainly in the para and ortho positions. The reaction according to FIGS. 1 and 2 involves two intermolecular electrophilic substitutions and one intramolecular electrophilic substitution (cyclization). More specifically, the reaction involves an intermolecular electrophilic substitution of a hydrogen of a phenyl group of a diphenyl ether molecule in the ortho position, followed by an intramolecular, 6-atom cyclization, of a hydrogen of the other phenyl group of this diphenyl ether molecule also in the ortho position, and also another intermolecular electrophilic substitution of a hydrogen of a phenyl group of another diphenyl ether molecule in the ortho position. The compound below is then obtained, of formula:

[Chem 15]

(V)

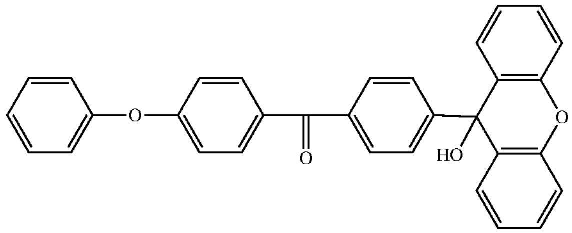

Since the —OH group of the compound of formula (V) is labile under acidic conditions, the carbocation below may be formed, of formula:

[Chem 16]

(VI)

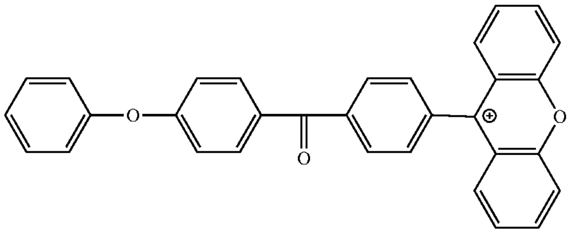

The reduced form of the carbocation of formula (VI) is the compound below, of formula:

[Chem 17]

(VII)

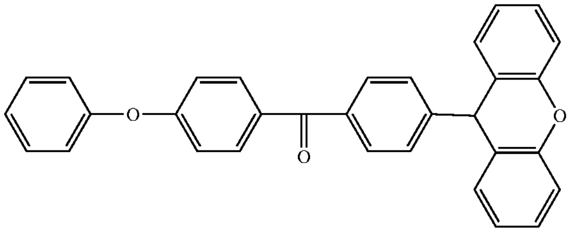

The main competing reaction to those shown in FIGS. 1 and 2 is that according to the reaction scheme in FIG. 3. As for FIGS. 1 and 2, FIG. 3 also illustrates the example of a mixture of diphenyl ether and terephthaloyl chloride in the presence of aluminum trichloride. The reaction according to FIG. 3 involves two intermolecular electrophilic substitutions of the hydrogen atom of a phenyl group in the para position of a diphenyl ether molecule. The compound below is thus also obtained, of formula:

[Chem 18]

(VIII)

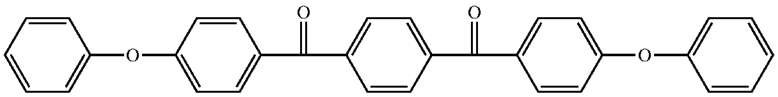

It is essential, in order for the 6-atom cyclization to take place, that the aromatic ether of formula (III) have a hydrogen atom in the ortho position of each phenyl group. Furthermore, it is also essential that the aromatic ether of formula (III) have a hydrogen atom in the para position of at least one phenyl group. The other positions of the phenyl groups of the aromatic ether of formula (III) may or may not be substituted.

Certain parameters may further favor the reaction for synthesizing the compound according to the invention (such as the reaction scheme according to FIG. 1 or FIG. 2) relative to competing reactions (mainly such as the reaction scheme according to FIG. 3).

These parameters may be intrinsic features of the reagents: the ortho and para positions of the aromatic ether (III) may be more or less activated depending on the nature and position of its possible substituents, due to their electron-donating or electron-withdrawing effect.

For example, for an aromatic ether of formula:

[Chem 19]

(III-x)

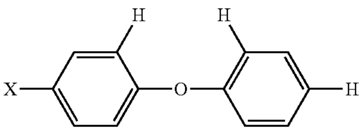

in which X is an electron-donating group, the electron-donating group X enables the activation of the phenyl bearing this group X (in bold), which promotes multiple substitutions on the aromatic rings.

These parameters may also be certain reaction variables as explained below in certain preferential embodiments.

In one embodiment, the reaction is performed without solvent. The reaction is then referred to as a bulk reaction.

In another embodiment, the reaction is performed in a reaction solvent. The reaction solvent is preferably a nonprotic solvent.

A protic solvent is a solvent containing at least one hydrogen atom bonded to an oxygen atom or to a nitrogen atom, and which is capable of donating protons to the reagents. Conversely, a nonprotic solvent is a solvent that is not a protic solvent.

The nonprotic solvent used herein may notably be chosen from methylene chloride, carbon disulfide, ortho-dichlorobenzene, meta-dichlorobenzene, para-dichlorobenzene, 1,2,4-trichlorobenzene, 1,2,3-trichlorobenzene, ortho-difluorobenzene, 1,2-dichloroethane, 1,1,2,2-tetrachloroethane, tetrachloroethylene, dichloromethane, nitrobenzene, and mixtures thereof. ortho-Dichlorobenzene is the solvent that is the most preferred.

The Lewis acids that may be used comprise, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride and molybdenum pentachloride. Aluminum trichloride, boron trichloride, aluminum tribromide, titanium tetrachloride, antimony pentachloride, ferric chloride, gallium trichloride and molybdenum pentachloride are preferred. Aluminum trichloride is particularly preferred.

The reaction between the compound of formula (III) and the compound of formula (IVa) or of formula (IVb) in the presence of a Lewis acid to manufacture a compound of formula (I) or (II) may be performed in a reactor. The reaction may be performed in a reactor. The reactor may be, for example, a glass reactor, a reactor with a glass inner wall or a reactor made of stainless metal materials, or lined with PTFE.

According to certain variants, the materials introduced into the reactor in the process of the invention are essentially, or consist of, the compound of formula (III), the compound of formula (IVa) or, respectively, of formula (IVb), the reaction solvent and the Lewis acid.

Preferentially, the reaction may be performed in a reaction mixture that substantially does not comprise any water.

Preferentially, the reaction may be performed in an atmosphere that substantially does not comprise any water or dioxygen, for example under a nitrogen or argon atmosphere.

The reaction mixture may be prepared by mixing together the components (compound of formula (III), compound of formula (IVa) or, respectively, of formula (IVb), Lewis acid and reaction solvent) in any order.

According to a first embodiment, an initial mixture is first prepared, comprising (and preferably consisting of) the compound of formula (III) and the compound of formula (IVa) or, respectively, of formula (IVb), in the reaction solvent. The initial mixture may notably be prepared by mixing together the three compounds, in any order. By way of example, the reaction solvent may be introduced into the reactor first, and the compounds of formula (III) and of formula (IVa) or, respectively, of formula (IVb) may then be added in turn. The Lewis acid is then added to the initial mixture.

Preferably, the Lewis acid is added in solid form. Alternatively, the Lewis acid may also be added in the form of a suspension or colloid, namely in the form of a heterogeneous mixture of solid Lewis acid particles in a solvent. The solvent for the suspension/colloid is advantageously the abovementioned reaction solvent. The Lewis acid may also be added in the form of a solution, namely in the form of a homogeneous mixture of Lewis acid in a solvent. The solvent of the solution is preferably the abovementioned reaction solvent.

According to a second embodiment, an initial mixture is first prepared, comprising (and preferably consisting of) the compound of formula (IVa) or, respectively, of formula (IVb), and the Lewis acid in the reaction solvent. The initial mixture may be prepared by mixing together the three compounds, in any order. The compound of formula (III) is then added to the initial mixture. It may be added in its liquid form or in the form of a solution, preferably in the abovementioned reaction solvent.

In a third embodiment, an initial mixture is first prepared comprising (and preferably consisting of) the compound of formula (III) and the Lewis acid in the reaction solvent. The initial mixture may be prepared by mixing together the three compounds, in any order. The compound of formula (IVa) or, respectively, of formula (IVb), is then added to the initial mixture. It may be added in solid or liquid form. Alternatively, it may be added in the form of a suspension, a colloid, or a solution, preferably in the abovementioned reaction solvent.

In certain embodiments:

- the molar amount of compound of formula (IVa) or, respectively, of formula (IVb), relative to the sum of the molar amounts of reaction solvent, compound of formula (III), compound of formula (IVa) or, respectively, of formula (IVb), and Lewis acid introduced into the reactor, is from 2% to 11%, and preferably 3% to 8%;

the molar amount of compound of formula (III), relative to the sum of the molar amounts of reaction solvent, compound of formula (III), compound of formula (IVa) or, respectively, of formula (IVb), and Lewis acid introduced into the reactor, is from 5% to 40%, and preferably from 8% to 25%;

the molar amount of Lewis acid, relative to the sum of the molar amounts of reaction solvent, compound of formula (III), compound of formula (IVa) or, respectively, of formula (IVb), and Lewis acid introduced into the reactor, is from 4% to 45%, and preferably from 8% to 30%;

the molar amount of compound of formula (III) relative to the molar amount of compound of formula (IVa) or, respectively, of formula (IVb), introduced into the reactor is from 2 to 6, and preferably from 2 to 4; and the molar amount of Lewis acid relative to the sum of the molar amounts of compound of formula (III) and of compound of formula (IVa) or, respectively, of formula (IVb), introduced into the reactor is from 0.25 to 2, and preferably from 0.3 to 1.5.

Preferably, the reaction mixture is stirred during at least part of the reaction step. Thus, the reactor is preferably equipped with a stirring device such as a mechanical stirrer (which may comprise, for example, one or more blades) or a recirculation loop comprising a pump.

The reaction step between the compound of formula (III) and the compound of formula (IVa) or, respectively, of formula (IVb), can be maintained, preferably with stirring, for a certain period of time, in order to complete the reaction to the desired extent.

Once the reaction is completed to the desired extent, the reaction mixture is referred to as the "product mixture". The product mixture comprises the desired product of formula:

[Chem 20]

(I)

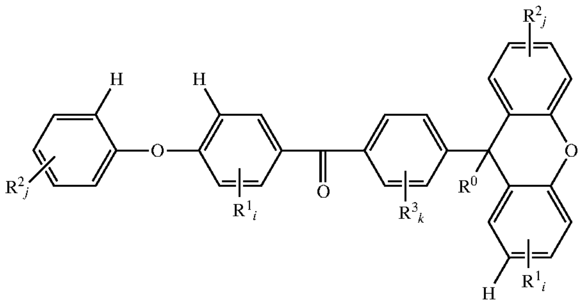

or, respectively, of formula:

[Chem 21]

(II)

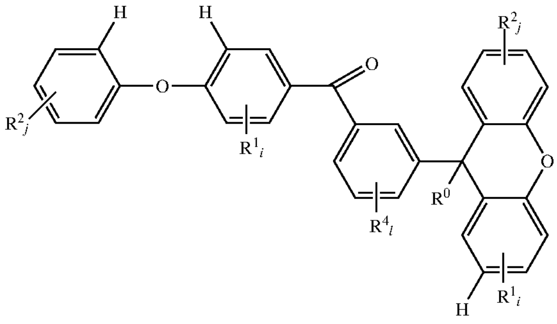

in which i, j, k, l, $R^1_i$, $R^2_j$, $R^3_k$ and $R^4_l$ are defined as described above for the compounds of formulae (III), (IVa) and (IVb).

Preferably, the temperature of the reaction mixture is less than or equal to 79° C. during at least a portion of the reaction. According to certain variants, the temperature of the reaction mixture is less than or equal to 55° C., or less than or equal to 50° C., or less than or equal to 40° C., or less than or equal to 30° C., or less than or equal to 20° C., or less than or equal to 10° C., or less than or equal to 5° C., or less than or equal to 0° C., or less than or equal to −5° C., or less than or equal to −10° C.

The temperature must notably remain below the boiling point of the reaction solvent. For this purpose, the reactor can, where appropriate, be operated under pressure, so that the temperature in the reactor can reach a higher value without boiling the solvent. In this case, the pressure in the reactor may range from 1 bar (atmospheric pressure) to 6 bar, preferably from 1.5 bar to 3 bar.

As a variant and preferably, the reaction may be performed at atmospheric pressure.

The temperature of the reaction mixture can remain almost constant during the reaction. Alternatively, it may vary during the reaction.

Once the reaction has been completed to the desired extent, the process according to the invention may comprise steps for recovering and purifying the compound of formula (I) or, respectively, of formula (II) from the product mixture. In addition to the desired product (I) or (II), the product mixture may notably contain the Lewis acid, possibly unreacted reagents and possibly product(s) derived from the competing reaction of the type shown in the reaction scheme according to FIG. 3.

In the embodiments in which the reagent of formula (IVa) is used, products derived from the competing reaction have the formula:

[Chem 22]

(IX-i)

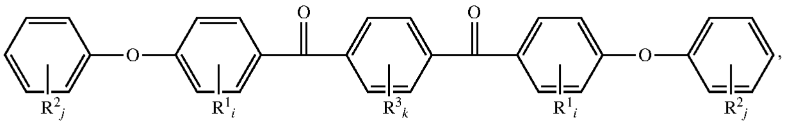

, and/or

[Chem 23]

(IX-ii)

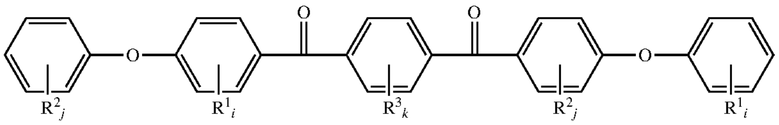

in which i, j, k, $R_i^1$, $R_j^2$ and $R_k^3$ and are defined as described above for the compounds of formulae (III) and (IVa).

In the embodiments in which the reagent of formula (IVb) is used, products derived from the competing reaction have the formula:

[Chem 24]

(X-i)

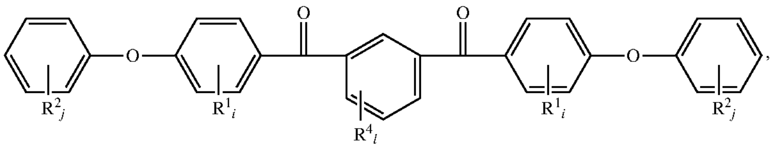

, and/or

[Chem 25]

(X-ii)

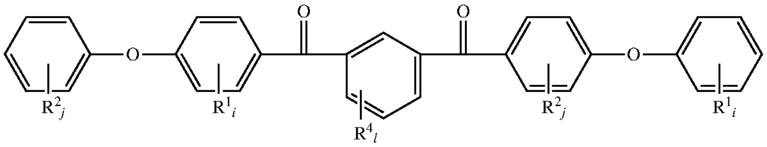

in which i, j, l, $R_i^1$, $R_j^2$ and $R_l^4$ are defined as described above for the compounds of formulae (III) and (IVb).

The competing reaction products of formulae (IX-i) and/or (IX-ii) or, respectively, of formula (X-i) and/or (X-ii) are generally less soluble in the reaction solvent than is the desired product of formula (I) or, respectively, of formula (II). Thus, whereas the desired reaction product is generally totally or virtually totally dissolved in the reaction solvent, the products derived from the competing reaction are generally at least partially in the form of a precipitate.

In order to promote the precipitation of the products derived from the competing reaction, the product mixture can be subjected to various treatments directed toward minimizing their solubility while at the same time having little or no effect on the solubility of the desired product.

In particular, the product mixture can be cooled. Preferably, the cooling rate may be, for example, from 1 to 10° C./hour, from 10 to 20° C./hour, or from 20 to 40° C./hour, or from 40 to 60° C./hour, or from 60 to 90° C./hour, or from 90 to 120° C./hour, or from 120 to 180° C./hour, or greater than 180° C./hour.

Alternatively, or additionally, the product mixture may be subjected to a shear stress.

Alternatively, or additionally, the product mixture may be subjected to removal by distilling off a portion of the reaction solvent.

Alternatively, or additionally, the product mixture may be subjected to the addition of a compound in solid form acting as a crystallization seed.

In certain embodiments, the product mixture may be placed in contact with a decomplexing solvent, the decomplexing solvent being a protic solvent. The decomplexing solvent enables the complexes formed with the Lewis acid to be dissociated, notably the complex formed with the desired product and the complexes formed with the products derived from the competing reaction.

The decomplexing solvent may be an organic solvent, such as methanol, acetic acid, formic acid, ethanol, isopropanol or benzyl alcohol. Methanol is preferred as organic solvent.

Alternatively, the decomplexing solvent may be an aqueous solution. The use of an aqueous solution as decomplexing solvent is particularly advantageous for two reasons. Firstly, an aqueous solution has a relatively high heat capacity. This enables better dissipation of the heat generated during the highly exothermic dissociation of the complexes formed with the Lewis acid. Secondly, the dissociated Lewis acid (in the form of an ionic salt, metal hydroxide, metal alkoxide, or any other compound resulting from the reaction of the Lewis acid with the decomplexing solvent) is soluble in the aqueous phase and can thus be recovered from the aqueous solution.

Mixtures of the above solvents may also be used, such as an aqueous-organic mixture, for example an aqueous solution mixed with methanol.

The aqueous solution may simply be water.

The aqueous solution may also be an acidic solution, such as a solution of hydrochloric acid, of phosphoric acid, of sulfuric acid, of nitric acid, of an organic acid such as formic acid and any combination thereof. In particular, the aqueous solution may be a hydrochloric acid solution. Preferably, the aqueous solution has a pH of less than 6, or less than 5, or less than 4, or less than 3, or less than 2, or less than 1, or less than 0. Preferably, the aqueous phase has a pH ranging from 1 to 2. In particular, the decomplexing solvent may be an aqueous solution containing hydrochloric acid at a concentration corresponding to such pH values. The aqueous solution may also be a basic solution, such as a solution of caustic sodium hydroxide, potassium hydroxide, calcium hydroxide, sodium carbonate, calcium carbonate, magnesium carbonate, potassium carbonate, ammonia or mixtures thereof. In these embodiments, the aqueous solution preferably has a pH of greater than 9, or greater than 10, or greater than 11, or greater than 12, or greater than 13, or greater than 14. Preferably, the decomplexing solvent has a pH ranging from 12 to 14.

In particular, the decomplexing solvent may be an aqueous solution containing NaOH at a concentration corresponding to such pH values.

In certain embodiments, a solid/liquid separation may be performed either directly on the product mixture obtained at the end of the reaction, or on the product mixture that has undergone one or more steps to promote the precipitation of products from competing reactions and/or a decomplexing step. A pasty cake and a liquid, in the form of at least one phase, are then obtained.

The temperature during the solid/liquid separation preferentially does not exceed 79° C. More preferably, the temperature during the solid/liquid separation does not exceed 60° C. Even more preferentially, the temperature during the solid/liquid separation does not exceed 30° C.

The solid/liquid separation may be performed in one or more successive steps, each step being chosen from the group consisting of: centrifugal filtration, sedimentation, centrifugal decantation, vacuum filtration, pressure filtration and gravity filtration.

In certain embodiments, the solid/liquid separation may comprise a step performed by centrifugal filtration, in a centrifugal filtration device. Specifically, it has been found that centrifugal filtration is particularly quick and efficient for performing the desired solid/liquid separation.

The centrifugal filtration device may notably have a horizontal or vertical axis.

The centrifugal filtration is preferably performed at an acceleration rate of from 2 to 1500×g, more preferably from 5 to 1000×g, and most particularly from 10 to 800×g.

Different acceleration values or ranges can be used in successive centrifugal filtration phases, such as a loading phase, a washing phase and/or a dewatering phase. For example, a low acceleration may be applied first, followed by a higher acceleration.

The pasty cake consists of wet solid material. It comprises in major amount the precipitated products derived from the competing reaction of formulae (IX-a) and/or (IX-b) or, respectively, of formulae (X-a) and/or (X-b) and in minor amount the desired reaction product of formula (I) or, respectively, of formula (II). Preferentially, the compound of formula (I) or, respectively, of formula (II) represents from 0.01 mol % to 10 mol % relative to the total number of moles of the compounds of formulae (I), (IX-i) and (IX-ii) or, respectively, of the compounds of formulae (II), (X-i) and (X-ii).

The liquid comprises in major amount the desired compound of formula (I) or (II) and in minor amount the products derived from the competing reaction of formulae (IX-a) and/or (IX-b) or, respectively, of formulae (X-a) and/or (X-b). In addition, the liquid may optionally comprise unreacted compounds, and/or synthetic intermediates. Preferentially, the compound of formula (I) or, respectively, of formula (II) represents from 90 mol % to 99.99 mol % relative to the total number of moles of the compounds of formulae (I), (IX-i) and (IX-ii) or, respectively, of the compounds of formulae (II), (X-i) and (X-ii).

In certain embodiments, it is possible to isolate the desired compound of formula (I) or formula (II) by means of various separation techniques that are known to those skilled in the art. For example, fractional or nonfractional distillation of the solvent(s) may be performed. Alternatively, displacement of the solvent with water by means of azeotropic distillation followed by filtration may be performed. Column separation of the various compounds is also a route of access to the compound of formula (I) or of formula (II).

The compound of formula (I) or, respectively, the compound of formula (II), notably in a form in which —$R_0$=—OH or —$R_0$=(+) (carbocation) or even —$R_0$=—H (for example, after reduction of the —OH group with an acid), may advantageously be used as a chromophore on account of its spectroscopic properties. It was shown that a pH of between 3 and 4 preferentially led to the —$R_0$=—OH form with a UV-visible absorbance band at 293 nm and that pH≤2 preferentially led to the —$R_0$=+ and/or —H form with an absorbance band shifted from 293 to 304 nm and also the appearance of three new bands at 380, 460 and 492 nm as illustrated in the spectrum.

According to certain embodiments, notably in embodiments in which the compound according to the invention includes reactive substituents, grafting of the chromophore to a biological molecule may be envisaged.

According to certain embodiments, the compound of formula (I) or, respectively, the compound of formula (II), in a form in which —$R_0$=—OH or —H, may be used as a free-radical generator. Such a free-radical generator may advantageously be used as an initiator of radical reactions, such as radical polymerization or grafting reactions.

Preferentially, the compound of formula (I) or, respectively, the compound of formula (II) is in a form in which —$R_0$=—OH.

According to certain embodiments, the compound of formula (I) or, respectively, the compound of formula (II) may be used as a photosensitive free-radical generator. It may thus be used as a photoinitiator, notably a UV photoinitiator, in a polymerization and/or crosslinking reaction. Applications in the field of resins, paints, inks or adhesives may be envisaged.

In particular, the compounds of formula (I) or of formula (II) according to the invention may advantageously replace more conventional photoinitiators, notably photoinitiators of the aminoacetophenone family (example: Irgacure 379 (2-(4-methylbenzyl)-2-(dimethylamino)-1-(4-morpholinophenyl) butan-1-one; CAS No. 119344-86-4) or SpeedCure BDMB (2-benzyl-2-dimethylamino-4-morpholinobutyrophenone; CAS No. 119313-12-1), which have absorption maxima in the region of 320 nm, or photoinitiators of the benzophenone family, for instance SpeedCure MBS (CAS No. 83846-85-9; benzoylmethyldiphenyl sulfide), which has a double maximum absorbance at 246 and 315 nm.

According to certain embodiments, the compound of formula (I) or, respectively, the compound of formula (II) may be used as a heat-sensitive free-radical generator. It may thus be used as a thermal initiator in a polymerization and/or crosslinking reaction.

In particular, in the field of performance materials, one of the approaches for extending the range of use of thermoplastics is to perform partial crosslinking of the polymer during its processing. On account of their aromatic nature, the compounds according to the invention have good affinity for aromatic and semiaromatic thermoplastic matrices, such as polyimides, polycarbonates, aromatic and semiaromatic polyamides, aromatic polysulfones, polyaryl ether ketones (for example polyether ketone ketone) and/or copolymers thereof. They can thus be readily added to such aromatic and semiaromatic thermoplastic matrices in such a way as to generate radicals during their processing and thus make it possible to ensure partial crosslinking of the thermoplastic matrix.

This crosslinking makes it possible, inter alia, to improve the high-temperature performance of the thermoplastic matrix, possibly in the presence of other chemical compounds. These properties are, for example, highly sought in the oil and gas industry (connectors, hoses, etc.).

Moreover, partial crosslinking makes it possible to limit, or even eliminate, the evolution of the crystallinity of semicrystalline thermoplastic matrices, generally observed in aging tests or when high temperatures are reached.

According to certain embodiments, the compound of formula (I) or, respectively, the compound of formula (II), in a form in which $—R_0$=—OH or —H, may be used as an adhesion promoter and/or coupling agent.

For example, it may be used in the field of thermoplastic composite materials. A thermoplastic composite material generally combines a thermoplastic matrix with reinforcing fibers (continuous or discontinuous). Sizing of the fibers is often necessary for the purpose of facilitating their handling, notably to limit abrasion between fibers, and for the purpose of ensuring a good interface between the reinforcing fibers and the matrix.

The application of the sizing may be performed in several ways but the preferred way is generally by forming an aqueous dispersion. On account of its aromatic nature, the compound according to the invention has good compatibility with carbon fibers, for example, and is also compatible with aromatic thermoplastic matrices: polyimide, polycarbonate, aromatic and semiaromatic polyamide, aromatic polysulfones, polyether aryl ketones, and copolymers thereof, thus affording good wettability.

After deposition of the aqueous dispersion and drying, during the placing in contact of the fibers with the matrix (by compounding, impregnation, coating, etc.), a free-radical grafting reaction of the compound according to the invention with the thermoplastic matrix can take place at the melting point of the thermoplastic matrix and thus ensure covalent bonding with the matrix.

EXAMPLES

The three examples below illustrate certain claims of this invention without limitation. The procedure followed is as follows:

In a first reactor equipped with mechanical stirring and under a stream of nitrogen directed toward a scrubber-type neutralization system, diphenyl ether (DPE) and terephthaloyl chloride (TCI) are introduced into 1,2-dichorobenzene (o-DCB) at room temperature. The table below shows the molar amounts for each reaction constituent for each example:

TABLE 1

| mole | Example 1 | Example 2 | Example 3 |
|---|---|---|---|
| DPE | 0.8 | 0.6 | 0.8 |
| TCl | 0.3 | 0.2 | 0.3 |
| oDCB | 5.5 | 5.5 | 4.0 |
| AlCl3 | 0.9 | 0.6 | 0.7 |

After dissolution, aluminum trichloride ($AlCl_3$) is slowly added at 25° C. (Example 1), 0° C. (Example 2) or 70° C. (Example 3), respectively. A step of maintaining the reaction medium at the same temperature for 3 hours then follows to complete the reaction. The reaction medium is then precipitated by transferring it into aqueous 3% hydrochloric acid solution at 50° C. After removing the aqueous aluminum phase, a precipitated reaction medium is obtained. A solid/liquid separation step follows using a pressurized filter with, on one side, the pasty cake essentially comprising the solid of the competing reaction, of formula VIII, and, on the other side, a filtrate which, after evaporation, makes it possible to isolate a mixture essentially comprising the targeted compound V. The mole ratios of compounds V and VIII in these mixtures were determined by $^1$H NMR analyses and are presented in the table below:

TABLE 2

| Mole ratio | Example 1 | Example 2 | Example 3 |
|---|---|---|---|
| Desired compound V | 94.8 | 90.4 | 93.5 |
| Compound VIII of competing reaction | 5.2 | 9.6 | 6.5 |

Characterizations

HPLC/MS

The mixture obtained according to Example 1, essentially containing the compound of formula (V), was analyzed by high pressure liquid chromatography (HPLC) using a Phenomenex Kinetex 2.6 μm C18 100A column coupled to mass spectrometry (MS-TOF) with an APCI (Atmospheric Pressure Chemical Ionization) ionization mode in positive mode. A characteristic peak at 6.3 minutes was thus observed, corresponding to the $[M+H]^+$ adduct of the compound of formula (V) (cf. FIG. 4).

The dehydrated form of the compound of formula (V), i.e. the compound of formula (VI) ($—R_0$=+, after protonation of the —OH function) corresponding to a particularly stable double-benzylic carbocation, was also observed with a peak at 7.7 minutes in acidic medium and confirmed by the adduct $[M+H—H_2O]^+$ in MS-TOF (cf. FIG. 5).

UV/IR

The absorbance of the compounds of formula (V) and of formula (VI), obtained from the mixture obtained according to Example 1 and essentially containing the compound of formula (V), was measured on a Cary 300 UV/Visible spectrophotometer in transmittance mode in a quartz cell at a concentration of 1 g/L after dilution in 1,2-dichlorobenzene.

FIG. 6 shows the absorbance band of the compound of formula (V), with an absorbance maximum at 293 nm.

It was observed that in acidic medium, i.e. at pH≤2, the form (VI) was favored leading to the shift of this absorbance band to an absorbance maximum at 304 nm and with the appearance of three new bands/shoulders having maxima at 380, 460 and 492 nm as shown in FIG. 7.

In FIG. 7, curve E1 represents the absorbance of a stock solution of the mixture obtained according to Example 1 at pH=4. Curve E2 represents the absorbance of the stock solution at pH=3. Curve E3 represents the absorbance of the stock solution at pH=2. Curve E4 represents the absorbance of the stock solution at a pH lower than that of E3. Curve E5 represents the absorbance of the stock solution to which twenty drops of a strong acid (pH<2) were added.

The invention claimed is:

1. A compound having the chemical formula:

(I)

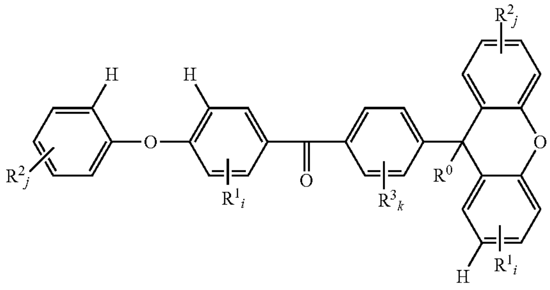

or (II)

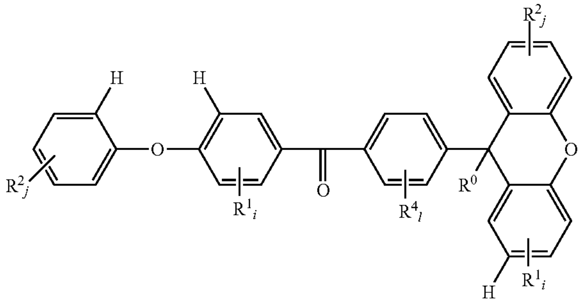

in which:

$R^0$ denotes: —H;

i, j, k and l are integers all equal to 0.

2. A method of analyzing a composition comprising a compound, comprising exposing the compound to light; and measuring at least one optical response of the compound, wherein the compound functions as a chromophore, and wherein the compound has the following chemical formula:

(I)

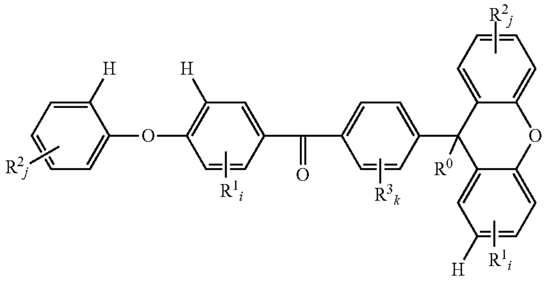

or (II)

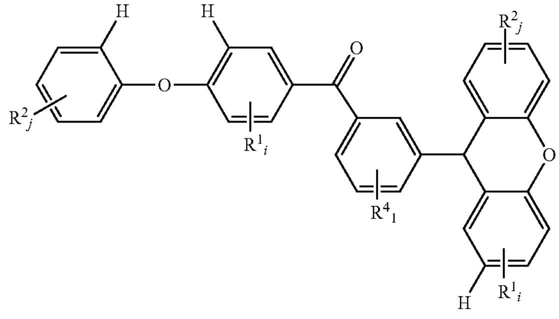

in which:

$R^0$ denotes: a charge +, —H, or —OH;

i, j, k and l are integers all equal to 0.

3. A method comprising generating free-radicals by activating a compound, wherein the compound has the following chemical formula:

(I)

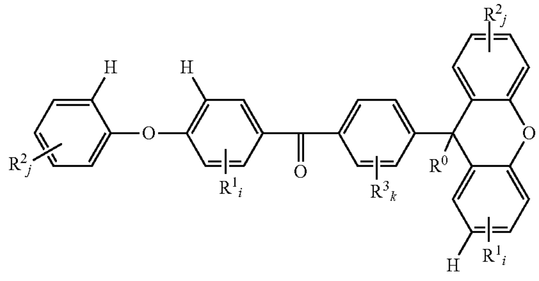

or (II)

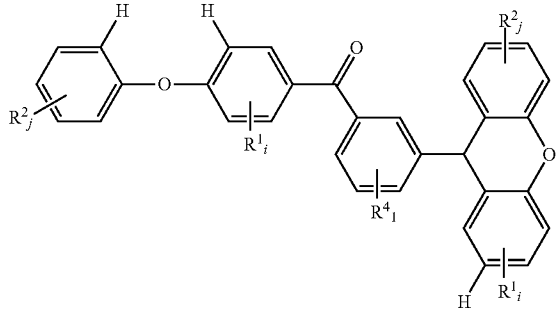

in which:

$R^0$ denotes: a charge +, —H, or —OH;

i, j, k and l are integers all equal to 0.

4. A method comprising promoting adhering and/or coupling to a substrate by applying a compound on a substrate, wherein the compound has the following chemical formula:

(I)

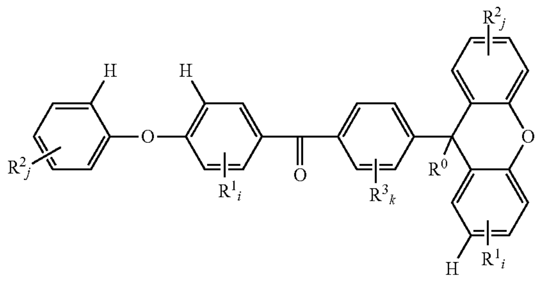

or

-continued (II)

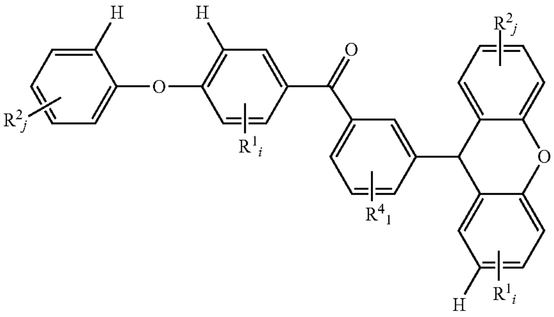

in which:

$R^0$ denotes: a charge +, —H, or —OH;

i, j, k and l are integers all equal to 0.

5. The method of claim 2, wherein $R^0$ denotes: —H.

6. The method of claim 3, wherein $R^0$ denotes: —H.

7. The method of claim 4, wherein $R^0$ denotes: —H.

* * * * *